United States Patent [19]

Oku et al.

[11] Patent Number: 5,061,718
[45] Date of Patent: Oct. 29, 1991

[54] BENZOTHIAZOLYLMETHOXY COMPOUNDS, PHARMACEUTICAL COMPOSITIONS COMPRISING THE SAME AND THEIR USE AS ANTI-INFLAMMATORY OR ANTI-ALLERGENIC AGENTS

[75] Inventors: Teruo Oku; Yoshio Kawai; Hiroshi Kayakiri; Kazuyoshi Kuratani; Masashi Hashimoto, all of Tsukuba, Japan

[73] Assignee: Fujisawa Pharmaceutical Company, Ltd., Osaka, Japan

[21] Appl. No.: 472,231

[22] Filed: Jan. 30, 1990

Related U.S. Application Data

[62] Division of Ser. No. 181,174, Apr. 13, 1988, Pat. No. 4,923,881.

[30] Foreign Application Priority Data

Apr. 28, 1987 [GB] United Kingdom ............. 8710008
Aug. 21, 1987 [GB] United Kingdom ............. 8719778
Jan. 15, 1988 [GB] United Kingdom ............. 8800872

[51] Int. Cl.$^5$ ............. A07D 277/62; A61K 31/425
[52] U.S. Cl. ............. 514/367; 546/152; 546/174; 546/180; 546/181; 546/339; 548/179; 548/180; 548/330; 568/630; 568/659
[58] Field of Search ............. 548/179, 180; 514/367

[56] References Cited

U.S. PATENT DOCUMENTS

| | | | |
|---|---|---|---|
| 4,567,184 | 1/1986 | Musser et al. | 546/149 |
| 4,661,596 | 4/1987 | Kreft et al. | 548/179 |
| 4,778,931 | 10/1988 | Musser et al. | 546/149 |
| 4,794,188 | 12/1988 | Musser et al. | 544/250 |

Primary Examiner—Mukund J. Shah
Assistant Examiner—Philip Datlow
Attorney, Agent, or Firm—Oblon, Spivak, McClelland, Maier & Neustadt

[57] ABSTRACT

The invention relates to an anti-inflammatory or antiallergic composition containing a compound of the formula

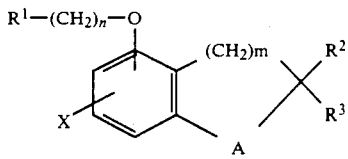

wherein
A is

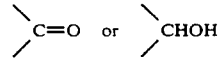

$R^1$ is aryl which may have cyano or carbamoyl, or heterocyclic group which may have lower alkyl,
$R^2$ is hydrogen or lower alkyl,
$R^3$ is lower alkyl,
X is hydrogen, halogen, hydroxy or lower alkyl,
m is an integer 1 or 2, and
n is an integer 1 to 4, or pharmaceutically acceptable salts thereof.

8 Claims, No Drawings

BENZOTHIAZOLYLMETHOXY COMPOUNDS, PHARMACEUTICAL COMPOSITIONS COMPRISING THE SAME AND THEIR USE AS ANTI-INFLAMMATORY OR ANTI-ALLERGENIC AGENTS

This is a division of application Ser. No. 07/181,174, filed on Apr. 13, 1988, now U.S. Pat. No. 4,923,881.

This invention relates to new bicyclic compounds and pharmaceutically acceptable salts thereof. More particularly, it relates to new bicyclic compounds and pharmaceutically acceptable salts thereof which have 5-lipoxygenase-inhibiting activity, to processes for the preparation thereof and to a pharmaceutical composition comprising the same.

The objective bicyclic compounds and pharmaceutically acceptable salts thereof are novel and can be represented by the following general formula (I):

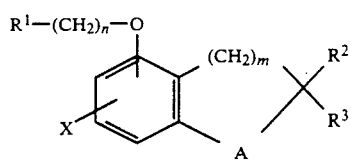

wherein
$A_1$ is

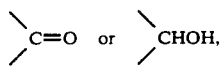

$R^1$ is aryl which may have cyano or carbamoyl, or heterocyclic group which may have lower alkyl,
$R^2$ is hydrogen or lower alkyl,
$R^3$ is lower alkyl,
X is hydrogen, halogen, hydroxy or lower alkyl,
m is an integer 1 or 2, and
n is an integer 1 to 4, and pharmaceutically acceptable salts thereof.

According to this invention, the new bicyclic compounds (I) can be prepared by various processes which are illustrated by the following schemes:

Process 1

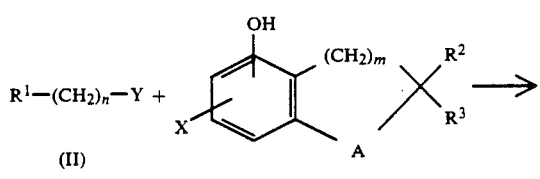

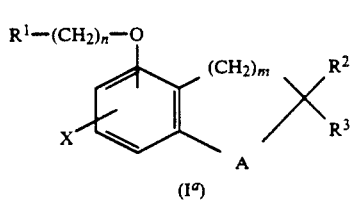

Process 2

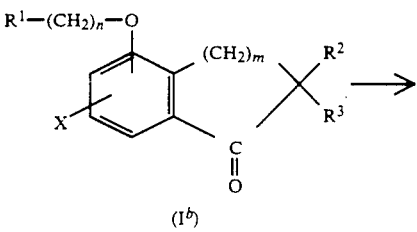

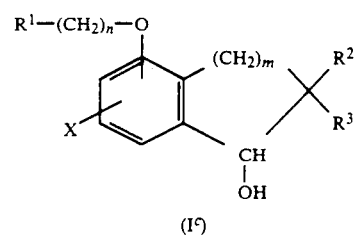

Process 3

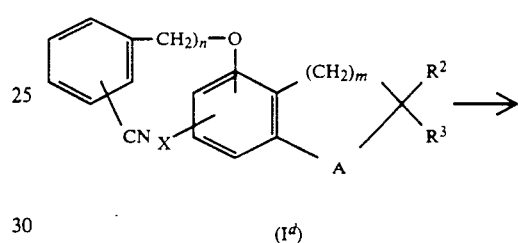

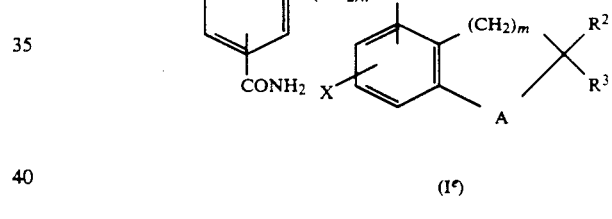

In the above formulae, Y is an acid residue and A, $R^1$, $R^2$, $R^3$, X, m and n are as defined before.

Preferred pharmaceutically acceptable salts of the object compound (I) are conventional non-toxic salts and may include a salt with an acid such as a salt with an inorganic acid (e.g., hydrochloride, hydrobromide, sulfate, phosphate, etc.), or a salt with an organic carboxylic or sulfonic acid (e.g., formate, acetate, trifluoroacetate, maleate, tartrate, methanesulfonate, benzenesulfonate, p-toluenesulfonate, etc.).

Preferred examples and illustrations of the various definitions, in the above descriptions, which the present invention includes within the scope thereof are explained in detail as follows.

The term "lower" is intended to mean 1 to 6 carbon atoms, unless otherwise indicated.

Preferred examples of "lower alkyl" may include a residue of straight and branched alkane having 1 to 6 carbon atom(s) such as methyl, ethyl, propyl, isopropyl, butyl, isobutyl, t-butyl, pentyl, neopentyl, hexyl and the like.

Preferred examples of "aryl" may include phenyl, tolyl, xylyl, naphtyl, 3-methyl-1,4-naphthalenedionyl and the like.

Preferred examples of "heterocyclic group" may include a unsaturated 3 to 8-membered monocyclic heterocyclic group containing 1 to 4 nitrogen atoms such as pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), and the like, a polycyclic (e.g. bicyclic) heterocyclic group containing at least one nitrogen atom such as indolyl, isoindolyl, indolizinyl benzimidazolyl, quinolyl, isoquinolyl and the like, a polycyclic (e.g. bicyclic) heterocyclic group containing at least one sulfur atom and at least one nitrogen atom such as benzothiazolyl, benzothiadiazolyl and the like, a polycyclic (e.g. bicyclic) heterocyclic group containing at least one oxygen atom such as benzofuranyl, isobenzofuranyl and the like. More preferred examples of "heterocyclic group" may include unsaturated benzene-fused 5 or 6-membered heterocyclic group containing one or two nitrogen atoms such as benzimidazolyl, quinolyl, isoquinolyl and the like.

Preferred examples of "halogen" is fluorine, chlorine, bromine and iodine.

Preferred examples of "acid residue" may include an acid residue of an inorganic acid (e.g. hydrochloric acid, hydrobromic acid, hydroiodic acid, sulfuric acid, etc.), an organic acid such as organic sulfonic acid (e.g. methanesulfonic acid, benzenesulfonic acid, toluenesulfonic acid, etc.), an organic carbamic acid (e.g. dimethylcarbamic acid, etc.) and the like.

Processes for preparing the object compound (I) of this invention are explained in detail in the following.

Process 1

This process relates to one for preparing the compound ($I^1$) or its salt by reacting the compound (II) or its salt with the compound (III).

Suitable salts of the compounds ($I^a$) and (II) may include the same as those exemplified as pharmaceutically acceptable salts of the compound (I) hereinbefore.

The reaction may be preferably conducted in the presence of a base. Suitable base may be an inorganic base such as alkali or alkaline earth metal hydroxide (e.g. sodium hydroxide, potassium hydroxide, calcium hydroxide, etc.), alkali metal bicarbonate (e.g. sodium bicarbonate, potassium bicarbonate, etc.), alkali or alkaline earth metal carbonate (e.g. sodium carbonate, potassium carbonate, calcium carbonate, etc.), alkali metal phosphate (e.g. sodium dihydrogenphosphate, potassium dihydrogenphosphate, disodium hydrogenphosphate, dipotassium hydrogenphosphate, etc.) or an organic base such as alkali metal alkoxide (e.g. sodium methoxide, potassium ethoxide, etc.), amines (e.g. triethylamine, pyridine, lutidine, etc.).

The reaction is usually conducted in conventional manner. For example, the reaction is preferably conducted under cooling, at ambient temperature or under heating, and in conventional solvent which does not have an adverse influence on the reaction such as acetone, methanol, ethanol, propanol, N,N-dimethylformamide or an optional mixture thereof.

Process 2

This process relates to one for preparing the compound ($I^c$) or its salt by reducing the compound ($I^b$) or its salt.

Suitable salts of the compounds ($I^b$) and ($I^c$) may include the same as exemplified as pharmaceutically acceptable salts of the compound (I) hereinbefore.

The reduction is conducted by a conventional method such as a catalytic reduction; a reduction using a combination of a metal such as iron, tin or zinc and an acid such as an inorganic acid (hydrochloric acid, sulfuric acid or the like) or an organic acid (acetic acid or the like); a combination of an alloy (e.g., sodium amalgam, aluminum amalgam, etc.), a metal (e.g., zinc, tin, iron, etc.) or a salt thereof (e.g., zinc chloride, stannous chloride, ferric or ferrous chloride, etc.) and water, an alkali solution or an alcohol (e.g., methanol, ethanol, propanol or butanol); a hydrazine compound (e.g., phenyl hydrazine or hydrazine); a combination of titanium chloride and hydrochloric acid; an alkali metal borohydride such as sodium borohydride, and potassium borohydride; lithium aluminium hydride; diborane, borane; or an electrolytic reduction.

Suitable examples of catalysts for the catalytic reduction are conventional ones.

In this reduction process, optically active compounds as an object compound ($I^c$) can be obtained by using as a reducing agent a combination of the above reducing agent and optically active ligands such as 4-anilino-3-methylamino-1-butanol, 2-amino-1,1-diphenyl-3-methylbutan-1-ol and the like.

The reaction conditions for this reduction, for example, the solvent to be used and the reaction temperature may optionally be selected in accordance with the reduction method to be used. In general, it is preferable to employ a solvent such as water, an alcohol such as methanol, ethanol and propanol, dioxane, acetonitrile tetrahydrofuran, dimethylformamide, pyridine and the like The reaction temperature is not particularly limited and the reaction is usually conducted under cooling, at ambient temperature or at an elevated temperature.

Process 3

This process relates to one for preparing the compound ($I^e$) by hydrolysing the compound ($I^d$).

In this hydrolysis reaction, all conventional methods used in the hydrolysis of the group "CN" to the group "$CONH_2$", are applicable.

The hydrolysis is preferably carried out in the presence of a base or an acid. Suitable bases may include the same as those exemplified in the preceding Process 1.

Suitable acids may include an organic acid (e.g. formic acid, acetic acid, propionic acid, etc.) and an inorganic acid (e.g. hydrochloric acid, hydrobromic acid, sulfuric acid, etc.).

The hydrolysis is more preferably carried out by the use of concentrated sulfuric acid; acetic acid and $BF_3$; $H_2O_2$ and $OH^-$; dry hydrochloric acid followed by $H_2O$.

This hydrolysis is usually carried out in an organic solvent, water or a mixed solvent thereof.

The reaction temperature is not critical and the reaction can usually be carried out at ambient temperature or under warming or heating around boiling point of the solvent.

Pharmaceutically acceptable salts of the compound (I) can be prepared by a conventional method, i.e., by treating the compound (I) with an acid. Preferred examples of said acid are the same as those exemplified in the explanation of pharmaceutically acceptable salts of the compound (I).

The starting compound (III) and its salt are novel and can be prepared, for example, according to Preparations as illustrated hereinafter or a similar manner thereto.

The object compound (I) includes stereoisomers such as optical isomers due to asymmetric carbon atom in the molecule, and such isomers are all subsumed in the scope of this invention.

The object compound, bicyclic compound (I) and pharmaceutically acceptable salts thereof of this invention have 5-lipoxygenase-inhibiting activity (inhibiting activity of SRS-A synthesis), and are useful as an antiallergic agent or an anti-inflammatory agent or the like for human being and animals, and more particularly are useful for treatment of asthma, psoriasis, hepatitis, pancreatitis, arthritis, nephritis, inflammatory bowel disease, septic shock, arteriosclerosis, myocardial infarction, cerebral vasospasm or the like.

In order to illustrate the usefulness of the object compound (I), the pharmacological test data of the representative compounds of the object compound (I) are shown below.

Test: Inhibitory Activity of SRS-A (Slow Reacting Substance of Anaphylaxis) synthesis in rat polymorpholeukocyte (PMN) of using the calcium ionophore (1) Materials and Methods:

Preparation of PMN from rat

Male Sprague-Dawley rats weighing 250-300 g were anesthetized with ether and each was injected intraperitoneally with 20 ml of 0.1% glycogen (from Oyster). After 20 hours the rats were sacrificed and PMN were recovered in rinse of the peritoneal cavity with 10 ml Dulbeccos PBS (components in g/L: $CaCl_2$ 0.1, $KH_2PO_4$ 0.2, $MgCl_2.6H_2O$ 0.1, NaCl 8.0, $Na_2HPO_4.7H_2O$ 2.16; pH7.4). These rinses were filtered through nylon wool filter and centrifuged for 5 min at 1000 xg. The pellet was suspended in Dulbeccos PBS and centrifuged for 5 min at 1000 xg. The pellet was resuspended in Dulbeccos PBS and adjusted the cell concentration to $10^7$ cells/ml with Dulbeccos PBS.

PMN stimulation

Samples were dissolved in ethanol and dispersed in Dulbeccos PBS to give a concentration of $10^{-10}-10^{-5}$M Antibiotic A23187; calcium ionophor (Dehring Diagnostics) (hereinafter referred to A23187) in DMSO(10mM) was diluted with Dulbeccos PBS to give the concentration of 1mM. Aliquots of the cell suspension ($1 \times 10^7$ cells/ml, 0.98 ml) were equilibrated for 30 min at 37° C. Solution of sample(10 μl) was added and incubated for 15 min at 37° C. before the addition of 10 μl of A23187 solution. Thus the final incubation volume of 1 ml contained approximately $1 \times 10^7$ cells, $10^{-10}-10^{-5}$M samples and 10 μM A23187. Incubation with A23187 were continued for 15 min at 37° C. The reactions were terminated by setting the assay tubes in ice bath to chill as rapidly as possible to 4° C. The test tubes were centrifuged at 1500 xg for 5 min at 4° C. and decanted the supernatants into the tubes and kept cold prior to assaying.

Determination of immunoreactive LTC4 (i-LTC4)

The concentration of i-LTC4 in the cell-free supernatants from the incubations were determined by specific radioimmunoassay. The mean values of i-LTC4 (these incubations were carried out in duplicate) of each sample were calculated and the effect of samples on the synthesis of the leukotrienes was presented as a percentage of the value in the absence of samples.

(2) Results:

| Test Compound (Example No.) | $IC_{50}$ (M) |
|---|---|
| 5 | $2.8 \times 10^{-7}$ |
| 6 | $8.7 \times 10^{-9}$ |
| 7 | $8.1 \times 10^{-8}$ |
| 8 | $1.6 \times 10^{-7}$ |
| 11 | $5.0 \times 10^{-8}$ |
| 12 | $1.2 \times 10^{-7}$ |
| 13 | $1.5 \times 10^{-8}$ |
| 14 | $4.2 \times 10^{-8}$ |
| 15 | $2.1 \times 10^{-7}$ |
| 16 | $3.7 \times 10^{-7}$ |
| 17 | $1.9 \times 10^{-6}$ |
| 19 | $1.1 \times 10^{-6}$ |
| 20 | $8.3 \times 10^{-8}$ |
| 21 | $4.3 \times 10^{-7}$ |
| 22 | $8.6 \times 10^{-7}$ |
| 23 | $1.1 \times 10^{-6}$ |
| 25 | $6.2 \times 10^{-7}$ |
| 26 | $2.1 \times 10^{-7}$ |
| 27 | $3.0 \times 10^{-7}$ |
| 33 | $1.4 \times 10^{-8}$ |
| 34 | $2.2 \times 10^{-9}$ |
| 35 | $6.5 \times 10^{-9}$ |
| 36 | $1.2 \times 10^{-7}$ |
| 37 | $2.5 \times 10^{-9}$ |
| 38 | $3.6 \times 10^{-7}$ |
| 39 | $6.4 \times 10^{-7}$ |
| 40 | $6.5 \times 10^{-9}$ |
| 41 | $5.6 \times 10^{-9}$ |

Pharmaceutical compositions of this invention can be used in a conventional pharmaceutical forms such as powders, fine granules, granules, tablets, dragee, microcapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 100 mg to 10 g as the object compound (I) or its pharmaceutically acceptable salt preferably 1 g to 5 g on the same basis, at the interval of 1 to 3 times a day. Typical unit doses may be 50 mg, 100 mg, 200 mg, 500 mg, 1 g and the like, although these are only examples and not limitative, of course.

The following Examples are given for the purpose of illustrating this invention.

Preparation 1

To a solution of lithium diisopropylamide prepared from n-butyllithium (4.0 ml, 1.56 M solution in n-hexane) and diisopropylamine (0.88 ml) in freshly distillated dimethoxyethane (20 ml) was added dropwise a solution of 3,4-dihydro-5-methoxy-1(2H)-naphthalenone (881 mg) in dimethoxyethane (5 ml) at −20° C. under nitrogen gas atmospheres. The mixture was stirred at −20°∼0° C. for 30 minutes and then warmed to 34° C. rapidly. To the mixture was added iodobutane (1.8 ml) in one portion. The resulting mixture was refluxed for 50 minutes, allowed to cool to ambient temperature and poured into aqueous saturated sodium bicarbonate solution (50 ml). The separated oil was extracted with ethyl acetate. The organic layer was washed successively with dilute aqueous hydrochloric acid, aqueous sodium bicarbonate solution and brine. The solvent was dried and evaporated in vacuo. The residue was purified by columnchromatography on silica gel (elution by chloroform/n-hexane, 1/10-1/6) to give 2,2-dibutyl-3,4-dihydro-5-methoxy-1(2H)-naphthalenone (255 mg) as a pale yellow syrup.

IR (CHCl$_3$): 2960, 2940, 1678, 1598, 1584, 1470, 1259 cm$^{-1}$

NMR (CDCl$_3$, δ): 0.88 (6H, t, J=6Hz), 1.10-1.38 (8H, m), 1.40-1.75 (4H, m), 2.02 (2H, t, J=6Hz), 2.47 (2H, t, J=6Hz), 3.88 (3H, s), 7.00 (1H, d, J=8Hz), 7.28 (1H, t, J=8Hz), 7.66 (1H, d, J=8Hz)

Preparation 2

A mixture of 2,2-dibutyl-3,4-dihydro-5-methoxy-1(2H)-naphthalenone (2.321 g) and aluminium bromide (7.0 g) in dried benzene (40 ml) was refluxed for 40 minutes and allowed to cool in an ice-water bath. The cooled mixture was poured into a mixture of 1N aqueous hydrochloric acid (150 ml) and diethyl ether (100 ml) with stirring. The organic layer was washed with brine, dried, and concentrated in vacuo to yield 2,2-dibutyl-3,4-dihydro-5-hydroxy-1(2H)-naphthalenone (2.643 g) as a crude syrup.

IR (CHCl$_3$): 3315, 2965, 2940, 1677, 1605, 1588 cm$^{-1}$

NMR (CDCl$_3$, δ): 0.89 (6H, t, J=6Hz), 1.10-1.38 (8H, m), 1.42-1.76 (4H, m), 2.06 (2H, t, J=6Hz), 2.87 (2H, t, J=6Hz), 5.10 (1H, s), 6.97 (1H, d, J=8Hz), 7.19 (1H, t, J=8Hz), 7.67 (1H, d, J=8Hz)

Preparation 3

To a solution of 2,2-dibutyl-3,4-dihydro-5-hydroxy-1(2H)-naphthalenone (9.59 g) in dry diethyl ether (100 ml) was added lithium aluminium hydride (1.33 g) slowly at 0° C. under a nitrogen atmosphere. The suspension was stirred for 3 hours at 0° C. and then poured into ice. The mixture was acidified with aqueous 1N hydrochloric acid and the separated oil was extracted with diethyl ether. The extract was washed with brine and aqueous sodium bicarbonate solution. The solvent was dried and concentrated in vacuo. The residue was purified by columnchromatography on silica gel (elution by CH$_2$Cl$_2$ and then 2% CH$_3$OH in CH$_2$Cl$_2$) to yield 2,2-dibutyl-5-hydroxy-1,2,3,4-tetrahydro-1-naphthol (9.05 g) as crystals.

mp: 82°-83° C.

IR (Nujol): 3400, 3100, 2930, 2850, 1585 cm$^{-1}$

NMR (CDCl$_3$, δ): 0.88 (3H, t, J=6Hz), 0.95 (3H, t, J=6Hz), 1.85-1.05 (15H, m), 2.48 (1H, m), 2.68 (1H, m), 4.33 (1H, br s), 4.93 (1H, s), 6.70 (1H, d, J=8Hz), 6.97 (1H, d, J=8Hz), 7.10 (1H, t, J=8Hz)

Following compounds were prepared according to a similar manner to that of Preparation 1.

Preparation 4

2,2-Dipropyl-3,4-dihydro-5-methoxy-1(2H)-naphthalenone (oil)

IR (CHCl$_3$): 2950, 2930, 2870, 1675, 1595, 1580, 1465, 1260 cm$^{-1}$

NMR (CDCl$_3$, δ): 0.90 (6H, t, J=7Hz), 1.15-1.75 (8H, m), 2.03 (2H, t, J=7Hz), 2.89 (2H, t, J=7Hz), 3.89 (3H, s), 7.02 (1H, d, J=8Hz), 7.29 (1H, t, J=8Hz), 7.68 (1H, d, J=8Hz)

Preparation 5

2,2-Dipentyl-3,4-dihydro-5-methoxy-1(2H)-naphthalenone (oil)

IR (CHCl$_3$): 2950, 2930, 2860, 1675, 1595, 1585, 1465, 1255 cm$^{-1}$

NMR (CDCl$_3$, δ): 0.87 (6H, t, J=7Hz), 1.10-1.75 (16H, m), 2.00 (2H, t, J=6Hz), 2.86 (2H, t, J=6Hz), 3.87 (3H, s), 6.99 (1H, d, J=8Hz), 7.26 (1H, t, J=8Hz), 7.65 (1H, d, J=8Hz)

Following compounds were prepared according to a similar manner to that of Preparation 2.

Preparation 6

2,2-Dipropyl-3,4-dihydro-5-hydroxy-1(2H)-naphthalenone mp: 98°-101° C.

IR (Nujol): 3280, 1665, 1600, 1585, 1580 cm$^{-1}$

NMR (CDCl$_3$, δ): 0.88 (6H, t, J=7Hz), 1.10-1.75 (8H, m), 2.05 (2H, t, J=7Hz), 2.90 (2H, t, J=7Hz), 5.98 (1H, br s), 7.02 (1H, d, J=8Hz), 7.17 (1H, t, J=8Hz), 7.64 (1H, d, J=8Hz)

Preparation 7

2,2-Dipentyl-3,4-dihydro-5-hydroxy-1(2H)-naphthalenone (oil)

IR (CHCl$_3$): 3320, 2950, 2930, 2850, 1675, 1600, 1585, 1460, 1275 cm$^{-1}$

NMR (CDCl$_3$, δ): 0.85 (6H, t, J=7Hz), 1.10-1.75 (16H, m), 2.05 (2H, t, J=6Hz), 2.89 (2H, t, J=6Hz), 7.00 (1H, d, J=8Hz), 7.18 (1H, t, J=8Hz), 7.64 (1H, d, J=8Hz)

Preparation 8

To a solution of 4-hydroxy-1-indanone (594 mg) and triethylamine (0.7 ml) in dry dichloromethane (10 ml) was added tert-butyldimethylsilyl chloride (724 mg) in several portions at 0° C. The mixture was stirred overnight at ambient temperature and then poured into a mixture of water (30 ml) and dichloromethane (20 ml). The separated organic layer was washed with 1N-hydrochloric acid, brine and aqueous saturated sodium bicarbonate solution, succeedingly. The solution was dried and evaporated in vacuo. The residue was purified by columnchromatography on silica gel eluted by dichloromethane to give 4-(tert-butyldimethylsilyl)oxy-1-indanone (1.002 g) as an oil.

IR (CHCl$_3$): 2950, 2930, 2860, 1705, 1695 cm$^{-1}$

NMR (CDCl$_3$, δ): 0.26 (6H, s), 1.04 (9H, s), 2.67 (2H, m), 3.03 (2H, m), 7.00 (1H, d, J=8Hz), 7.37 (1H, t, J=8Hz), 7.48 (1H, d, J=8Hz)

Preparation 9

A mixture of 4-(tert-butyldimethylsilyl)oxy-1-indanone (524 mg), 1-iodobutane (0.91 ml), and potassium tert-butoxide (896 mg) in dry benzene (15 ml) was refluxed for 2 hours under nitrogen. The reaction mixture was allowed to cool and poured into water. The separated oil was extracted with ethyl acetate. The organic layer was washed with brine, and concentrated in vacuo. The residue was subjected to columnchromatography on silica gel (elution by 10% n-hexane in dichloromethane and then dichloromethane) to yield 2,2-dibutyl-4-hydroxy-1-indanone (150 mg) as crystals.

mp: 114°-115° C.

IR (CHCl$_3$): 3300, 2950, 2930, 2855, 1695, 1595 cm$^{-1}$

NMR (CDCl$_3$, δ): 0.84 (6H, t, J=7Hz), 0.95-1.35 (8H, m), 1.50-1.75 (4H, m), 2.93 (2H, s), 5.70 (1H, br s), 7.07 (1H, d, J=8Hz), 7.28 (1H, t, J=8Hz), 7.36 (1H, d, J=8Hz)

Preparation 10

To a solution of lithium diisopropylamide prepared from n-butyllithium (4.0 ml, 1.56 M solution in n-hexane) and diisopropylamine (0.88 ml) in freshly distillated dimethoxyethane (20 ml) was added dropwise a solution of 3,4-dihydro-5-methoxy-1(2H)-naphthalenone (881 mg) in dimethoxyethane (5 ml) at −20° C. under N$_2$ gas atmosphere. The mixture was stirred at −20~0° C. for half an hour and then warmed to 34° C. rapidly. To the mixture was added iodobutane (1.8 ml) in one portion. The mixture was refluxed for 50 minutes, allowed to cool to ambient temperature and poured into aqueous saturated sodium bicarbonate solution (50 ml). The separated oil was extracted with ethyl acetate. The organic layer was washed with dilute aqueous hydrochloric acid, aqueous sodium bicarbonate solution, and brine succeedingly. The solvent was dried and evaporated in vacuo.

The residue was purified by column chromatography on silica gel (elution by chloroform/n-hexane, 1/10 - 1/6) to give 2-butyl-3,4-dihydro-5-methoxy-1(2H)-naphthalenone (309 mg) as a pale yellow oil.

NMR (CDCl$_3$, δ): 0.92 (3H, t, J=6Hz), 1.20-1.55 (5H, m), 1.72-2.00 (2H, m), 2.25 (1H, m), 2.45 (1H, m), 2.75 (1H, ddd, J=18, 10, 6Hz), 3.05 (1H, d, t, J=18, 6Hz), 3.88 (3H, s), 7.00 (1H, d, J=8Hz), 7.28 (1H, t, J=8Hz), 7.64 (1H, d, J=8Hz)

Preparation 11

2-Butyl-3,4-dihydro-7-methoxy-1(2H)-naphthalenone (oil) was prepared according to a similar manner to that of Preparation 10.

NMR (CDCl$_3$, δ): 0.92 (3H, t, J=7Hz), 1.25-1.60 (5H, m), 1.75-2.05 (2H, m), 2.22 (1H, m), 2.43 (1H, m), 2.88-2.96 (2H, m), 3.84 (3H, s), 7.04 (1H, dd, J=3, 9Hz), 7.15 (1H, d, J=9Hz), 7.51 (1H, d, J=3Hz)

Preparation 12

2,2-Dibutyl-3,4-dihydro-7-methoxy-1(2H)-naphthalenone (oil) was prepared according to a similar manner to that of Preparation 1.

IR (CHCl$_3$): 2960, 2940, 1675, 1609, 1499 cm$^{-1}$

NMR (CDCl$_3$, δ): 0.88 (6H, t, J=7Hz), 1.08-1.80 (12H, m), 2.01 (2H, t, J=6Hz), 2.89 (2H, t, J=6Hz), 3.83 (3H, s), 7.03 (1H, dd, J=3, 9Hz), 7.07 (1H, d, J=9Hz), 7.53 (1H, d, J=3Hz)

Following compounds were prepared according to a similar manner to that of Preparation 2.

Preparation 13

2-Butyl-3,4-dihydro-5-hydroxy-1(2H)-naphthalenone (oil).

IR (CHCl$_3$): 3350, 2920, 1660, 1603, 1495 cm$^{-1}$

NMR (CDCl$_3$, δ): 0.92(3H, t, J=6Hz), 1.15-1.70 (5H, m), 1.80-2.05 (2H, m), 2.38 (1H, m), 2.48 (1H, m), 2.78 (1H, dq, J=18, 5Hz), 3.03 (1H, d, t, J=18, 5Hz), 5.14 (1H, br s), 6.97 (1H, d, J=8Hz), 7.18 (1H, t, J=8Hz), 7.65 (1H, d, J=8Hz)

Preparation 14

2-Butyl-3,4-dihydro-7-hydroxy-1(2H)-naphthalenone (oil)

NMR (CDCl$_3$, δ): 0.93 (3H, t, J=6Hz), 1.20-2.10 (7H, m), 2.23 (1H, m), 2.47 (1H, m), 2.92 (2H, t, J=6Hz), 6.25 (1H, br s), 7.03 (1H, dd, J=2, 10Hz), 7.15 (1H, d, J=10Hz), 7.63 (1H, d, J=2Hz)

Preparation 15

2,2-Dibutyl-3,4-dihydro-7-hydroxy-1(2H)-naphthalenone (oil)

IR (CHCl$_3$): 3320, 2930, 1668, 1599, 1581 cm$^{-1}$

NMR (CDCl$_3$, δ): 0.88 (6H, t, J=7Hz), 1.05-1.35 (8H, m), 1.40-1.80 (4H, m), 2.02 (2H, t, J=6Hz), 2.88 (2H, t, J=6Hz), 5.60 (1H, br s), 7.00 (1H, d, J=8Hz), 7.11 (1H, d, J=8Hz), 7.60 (1H, s)

EXAMPLE 1

A mixture of 2,2-dibutyl-3,4-dihydro-5-hydroxy-1(2H)-naphthalenone (2.643 g), 2-chloromethylquinoline (1.7 g), and potassium carbonate (1.67 g) in N,N-dimethylformamide (16 ml) was stirred at 80° C. for 4 hours. The cooled mixture was poured into water. The separated oil was extracted with ethyl acetate. The ethyl acetate layer was washed with water, dried, and concentrated in vacuo. The crude product was chromatographed on silica gel using 25% ethyl acetate in n-hexane as eluent to yield 2,2-dibutyl-3,4-dihydro-5-(2-quinolylmethoxy)-1(2H)-naphthalenone (3.09 g) as a pale yellow syrup.

IR (CHCl$_3$): 2960, 2940, 1679, 1600, 1582 1468 cm$^{-1}$

NMR (CDCl$_3$, δ): 0.89 (6H, t, J=6Hz), 1.10-1.40 (8H, m), 1.47-1.75 (4H, m), 2.06 (2H, t, J=6Hz), 3.03 (2H, t, J=6Hz), 5.42 (2H, s), 7.09 (1H, d, J=8Hz), 7.24 (1H, t, J=8Hz), 7.57 (1H, t, J=8Hz), 7.67-7.80 (3H, m), 7.85 (1H, d, J=8Hz), 8.09 (1H, d, J=8Hz), 8.23 (1H, d, J=8Hz)

Following compounds were prepared according to a similar manner to that of Example 1.

EXAMPLE 2

2,2-Dipropyl-3,4-dihydro-5-(2-quinolylmethoxy)-1(2H)-naphthalenone (oil)

IR (CHCl$_3$): 2950, 2930, 2860, 1675, 1595, 1580, 1465, 1260 cm$^-$

NMR (CDCl$_3$, δ): 0.89 (6H, t, J=7Hz), 1.10-1.75 (8H, m), 2.07 (2H, t, J=6Hz), 3.03 (2H, t, J=6Hz), 5.42 (2H, s), 7.09 (1H, d, J=8Hz), 7.23 (1H, t, J=8Hz), 7.57 (1H, t, J=8Hz), 7.65-7.80 (3H, m), 7.86 (1H, d, J=8Hz), 8.10 (1H, d, J=8Hz), 8.23 (1H, d, J=8Hz)

EXAMPLE 3

2,2-Dipentyl-3,4-dihydro-5-(2-quinolylmethoxy)-1(2H)-naphthalenone (oil)

IR (CHCl$_3$): 2950, 2930, 2850, 1675, 1595, 1580, 1465, 1260 cm$^{-1}$

NMR (CDCl$_3$, δ): 0.89 (6H, t, J=7Hz), 1.10-1.75 (16H, m), 2.09 (2H, t, J=6Hz), 3.06 (2H, t, J=6Hz), 5.24 (2H, s), 7.11 (1H, d, J=8Hz), 7.27 (1H, t, J=8Hz), 7.60 (1H, t, J=8Hz), 7.65-7.85 (3H, m), 7.88 (1H, d, J=8Hz), 8.11 (1H, d, J=8Hz), 8.26 (1H, d, J=8Hz)

EXAMPLE 4

2,2-Dibutyl-4-(2-quinolylmethoxy)-1-indanone (oil)

IR (CHCl$_3$): 2950, 2930, 2860, 1700, 1595, 1485, 1265 cm$^{-1}$

NMR (CDCl$_3$, δ): 0.85 (6H, t, J=7Hz), 1.10-1.40 (8H, m), 1.50-1.80 (4H, m), 3.04 (2H, s), 5.48 (2H, s), 7.13 (1H, d, J=8Hz), 7.30-7.40 (2H, m), 7.58 (1H, t, J=8Hz), 7.72 (1H, d, J=8Hz), 7.78 (1H, t, J=8Hz), 7.87 (1H, d, J=8Hz), 8.11 (1H, d, J=8Hz), 8.25 (1H, d, J=8Hz)

EXAMPLE 5

2,2-Dibutyl-4-(2-quinolylmethoxy)-1-indanone hydrochloride was prepared by treating 2,2-dibutyl-4-(2-quinolylmethoxy)-1-indanone with hydrogen chloride in ethyl ether.

mp: 162°-165° C.

IR (Nujol): 2400, 1720, 1605, 1485, 1415 cm$^{-1}$

NMR (CDCl$_3$, δ): 0.86 (6H, t, J=7Hz), 1.00-1.40 (8H, m), 1.50-1.75 (4H, m), 3.03 (2H, s), 6.09 (2H, s), 7.25-7.50 (3H, m), 7.39 (1H, t, J=8Hz), 8.05-8.25 (3H, m), 8.88 (1H, d, J=8Hz), 9.00 (1H, d, J=8Hz)

EXAMPLE 6

To a solution of 2,2-dibutyl-3,4-dihydro-5-(2-quinolylmethoxy)-1(2H)-naphthalenone (500 mg) in methanol (20 ml) was added sodium borohydride (68 mg) with stirring in an ice bath. The mixture was stirred for half an hour in an ice bath and then sodium borohydride (136 mg) was added thereto at the same temperature. The solution was stirred for 1.5 hours at ambient temperature, followed by the addition of sodium borohydride (68 mg). The mixture was stirred at ambient temperature for half an hour and then poured into water with stirring in an ice bath. The separated solid was collected by filtration, washed with water (50 ml), dried, and recrystallized from methanol to yield 2,2-dibutyl-5-(2-quinolylmethoxy)-1,2,3,4-tetrahydro-1-naphthol (388 mg).

mp: 122°-123° C.

IR (CHCl$_3$): 3300, 2949, 2930, 1600, 1584, 1465 cm$^{-1}$

NMR (CDCl$_3$, δ): 0.88 (3H, t, J=6Hz), 0.95 (3H, t, J=6Hz), 1.08-1.84 (15H, m), 2.63 (1H, m), 2.92 (1H, m), 4.35 (1H, d, J=6Hz), 5.38 (2H, s), 6.85 (1H, d, J=8Hz), 7.02 (1H, d, J=8Hz), 7.26 (1H, t, J=8Hz), 7.55 (1H, t, J=8Hz), 7.71-7.79 (2H, m), 7.84 (1H, d, J=8Hz), 8.08 (1H, d, J=8Hz), 8.21 (1H, d, J=8Hz)

EXAMPLE 7

A mixture of 2,2-dibutyl-5-hydroxy-1,2,3,4-tetrahydro-1-naphthol (232 mg), 2-chloromethylpyridine (118 mg), and potassium carbonate (128 mg) in N,N-dimethylformamide (2 ml) was stirred at 70° C. for 5 hours. To the cooled mixture, was added water (5 ml) in an ice-water bath. The supernatant was discarded. The residual gum was dissolved in ethyl acetate (15 ml , dried over magnesium sulfate and concentrated in vacuo to give a brown syrup (358 mg). The residual syrup was powderlized in an ice-water bath and recrystallized from n-hexane to yield 2,2-dibutyl-5-(2-pyridylmethoxy)-1,2,3,4-tetrahydro-1-naphthol (190 mg) as a slightly brownish powder.

mp: 106°-107° C.

IR (CHCl$_3$): 3320, 2935, 1585 cm$^{-1}$

NMR (CDCl$_3$, δ): 0.88 3H, t, J=7Hz), 0.95 (3H, t, J=7Hz), 1.06-1.90 15H, m), 2.58 (1H, m), 2.88 (1H, m), 4.34 (1H, d, J=5Hz), 5.52 (2H, s), 6.81 (1H, d, J=8Hz), 7.01 (1H, d, J=8Hz), 7.18 (1H, t, J=8Hz), 7.25 (1H, m), 7.57 (1H, d, J=7Hz), 7.75 (1H, t, J=7Hz), 8.59 (1H, d, J=5Hz)

EXAMPLE 8

To a solution of 2,2-dibutyl-5-(2-cyanobenzyloxy)-1,2,3,4-tetrahydro-1-naphthol (500 mg) in a mixture of ethanol (3.5 ml) and aqueous 6N-sodium hydroxide solution (0.275 ml) was added aqueous 30% hydrogen peroxide (2.62 ml) in one portion at ambient temperature. The mixture was stirred for 5 hours at 50° C. and allowed to stand overnight at ambient temperature. The reaction mixture was diluted with ethyl acetate (40 ml). The separated organic layer was washed with aqueous hydrochloric acid, aqueous sodium bicarbonate solution, and brine, and then dried, and evaporated under reduced pressure. The residue was crystallized from aqueous ethanol to yield 2,2-dibutyl-5-(2-carbamoylbenzyloxy)-1,2,3,4-tetrahydro-1-naphthol (425 mg).

mp: 73°-75° C.

IR (CHCl$_3$): 3480, 3400, 2910, 1665, 1580 cm$^{-1}$

NMR (CDCl$_3$, δ): 0.86 (3H, t, J=7Hz), 0.93 (3H, t, J=7Hz), 1.03-1.80 (15H, m), 2.47 (1H, m), 2.76 (1H, m), 4.33 (1H, s), 5.27 (2H, s), 5.77 (1H, br s), 6.38 (1H, br s), 6.90 (1H, d, J=8Hz), 7.03 (1H, d, J=8Hz), 7.20 (1H, t, J=8Hz), 7.41 (1H, t, J=8Hz), 7.51 (1H, t, J=8Hz), 7.62 (1H, d, J=8Hz), 7.68 (1H, d, J=8Hz)

Following compounds were prepared according to a similar manner to that of Example 7.

EXAMPLE 9

2,2-Dibutyl-5-(4-cyanobenzyloxy)-1,2,3,4-tetrahydro-1-naphthol (oil)

IR (Nujol): 3450, 2310, 1590, 1260 cm$^{-1}$

NMR (CDCl$_3$, δ): 0.88 (3H, t, J=8.1Hz), 0.97 (3H, t, J=8.1Hz), 1.20-1.82 (15H, m), 2.45-2.40 (2H, m), 4.35 (1H, s), 5.14 (2H, s), 6.77 (1H, d, J=8.5Hz), 7.04 (1H, d, J=8.5Hz), 7.18 (1H, d, J=8.5Hz), 7.58 (2H, d, J=8.5Hz), 7.69 (2H, d, J=8.5Hz)

EXAMPLE 10

2,2-Dibutyl-5-(2-cyanobenzyloxy)-1,2,3,4-tetrahydro-1-naphthol mp: 112°-113° C.

IR (CHCl$_3$): 3580, 2920, 2210, 1581 cm$^{-1}$

NMR (CDCl$_3$, δ): 0.87 (3H, t, J=7Hz), 0.94 (3H, t, J=7Hz), 1.10-1.82 (15H, m), 2.55 (1H, m), 2.85 (1H, m), 4.35 (1H, s), 5.27 (2H, s), 6.85 (1H, d, J=8Hz), 7.05 (1H, d, J=8Hz), 7.21 (1H, t, J=8Hz), 7.44 (1H, t, J=8Hz), 7.73-7.61 (3H, m)

EXAMPLE 11

2,2-Dibutyl-5-(2-benzothiazolylmethoxy)-1,2,3,4-tetrahydro-1-naphthol mp: 124°-125° C.

IR (CHCl$_3$): 3350, 2940, 1583 cm$^{-1}$

NMR (CDCl$_3$, δ): 0.88 3H, t, J=7Hz , 0.95 (3H, t, J=7Hz), 1.08-1.86 (15H, m), 2.60 (1H, m), 2.90 (1H, m), 4.35 (1H, s), 5.48 (2H, s), 6.86 (1H, d, J=8Hz), 7.06 (1H, d, J=8Hz), 7.20 (1H, t, J=8Hz), 7.41 (1H, t, J=8Hz), 7.51 (1H, t, J=8Hz), 7.91 (1H, d, J=8Hz), 8.03 (1H, d, J=8Hz)

EXAMPLE 12

2,2-Dibutyl-5-(4-pyridylmethoxy)-1,2,3,4-tetrahydro-1-naphthol mp: 139°-140° C.

IR (Nujol): 3170, 1605, 1585, 1560 cm$^{-1}$

NMR (CDCl$_3$, δ): 0.88 (3H, t, J=7Hz), 0.94 (3H, t, J=7Hz), 1.85-1.05 (15H, m), 2.57 (1H, m), 2.85 (1H, m), 4.35 (1H, s), 5.10 (2H, s), 6.75 (1H, d, J=8Hz), 7.03 (1H, d, J=8Hz), 7.19 (1H, t, J=8Hz), 7.40 (2H, d, J=6Hz), 8.61 (2H, d, J=6Hz)

Following compounds were prepared according to a similar manner to that of Example 6.

EXAMPLE 13

2,2-Dipropyl-5-(2-quinolylmethoxy)-1,2,3,4-tetrahydro-1-naphthol mp: 137°–138° C.

IR (Nujol): 3200, 1600, 1585, 1375, 1265 cm$^{-1}$

NMR (CDCl$_3$, δ): 0.88 (3H, t, J=7Hz), 0.96 (3H, t, J=7Hz), 1.10–1.85 (11H, m), 2.63 (1H, m), 2.91 (1H, m), 4.35 (1H, d, J=6Hz), 5.38 (2H, s), 6.86 (1H, d, J=8Hz), 7.01 (1H, d, J=8Hz), 7.18 (1H, t, J=8Hz), 7.55 (1H, t, J=8Hz), 7.71 (1H, d, J=8Hz), 7.75 (1H, t, J=8Hz), 7.85 (1H, d, J=8Hz), 8.09 (1H, d, J=8Hz), 8.21 (1H, d, J=8Hz)

EXAMPLE 14

2,2-Dipentyl-5-(2-quinolylmethoxy)-1,2,3,4-tetrahydro-1-naphthol mp: 98°–98.5° C.

IR (Nujol): 3200, 1600, 1585, 1570, 1505 cm$^{-1}$

NMR (CDCl$_3$, δ): 0.86 (3H, t, J=7Hz), 0.92 (3H, t, J=7Hz), 1.05–1.85 (19H, m), 2.62 (1H, m), 2.90 (1H, m), 4.34 (1H, d, J=5Hz), 5.39 (2H, s), 6.84 (1H, d, J=8Hz), 7.01 (1H, d, J=8Hz), 7.16 (1H, t, J=8Hz), 7.55 (1H, t, J=8Hz), 7.80–7.65 (2H, m), 7.85 (1H, d, J=8Hz), 8.09 (1H, d, J=8Hz), 8.22 (1H, d, J=8Hz)

EXAMPLE 15

2,2-Dibutyl-4-(2-quinolylmethoxy)-1-indanol mp: 82°–83° C.

IR (Nujol): 3350, 1595, 1480, 1275 cm$^{-1}$

NMR (CDCl$_3$, δ): 0.91 (6H, t, J=7Hz), 1.10–1.80 (13H, m), 2.71 (1H, d, J=17Hz), 2.90 (1H, d, J=17Hz), 4.81 (1H, d, J=7Hz), 5.40 2H, s), 6.81 (1H, d, J=8Hz), 7.00 (1H, d, J=8Hz), 7.15 (1H, t, J=8Hz), 7.55 (1H, t, J=8Hz), 7.67 (1H, d, J=8Hz), 7.75 (1H, t, J=8Hz), 7.84 (1H, d, J=8Hz), 8.08 (1H, d, J=8Hz), 8.20 (1H, d, J=8Hz)

EXAMPLE 16

2,2-Dibutyl-5-(4-carbamoylbenzyloxy)-1,2,3,4-tetrahydro-1-naphthol was prepared according to a similar manner to that of Example 8.

mp: 164°–165° C.

IR (Nujol): 3425, 1685, 1590, 1265 cm$^{-1}$

NMR (CDCl$_3$, δ): 0.88 (3H, t, J=7.2Hz), 0.97 (3H, t, J=7.2Hz), 1.19–1.45 (15H, m), 1.50–1.81 (2H, m), 2.46–2.90 (2H, m), 4.35 (1H, s), 5.14 (2H, s), 6.11 (2H, s), 6.79 (1H, d, J=8.3Hz), 7.03 (1H, d, J=8.3Hz), 7.16 (1H, d, J=8.3Hz), 7.53 (2H, d, J=8.2Hz), 7.86 (2H, d, J=8.2Hz)

Following compounds were prepared according to a similar manner to that of Example 1.

EXAMPLE 17

2-Butyl-3,4-dihydro-5-(2-quinolylmethoxy)-1(2H)-naphthalenone mp: 97°–98° C.

IR (CHCl$_3$) 2950, 1678, 1598, 1580 cm$^{-1}$

NMR (CDCl$_3$, δ): 0.93 (3H, t, J=7Hz), 1.20–1.60 (5H, m), 1.80–2.03 (2H, m), 2.30 (1H, m), 2.50 (1H, m), 2.93 (1H, dq, J=18, 5Hz), 3.23 (1H, dt, J=18, 5Hz), 5.42 (2H, s), 7.09 (1H, d, J=8Hz), 7.23 (1H, t, J=8Hz), 7.57 (1H, t, J=8Hz), 7.63–7.83 (3H, m), 7.85 (1H, d, J=8Hz), 8.09 (1H, d, J=8Hz), 8.22 (1H, d, J=8Hz)

EXAMPLE 18

2-Butyl-3,4-dihydro-7-(2-quinolylmethoxy)-1(2H)-naphthalenone (oil)

IR (CHCl$_3$): 2950, 2925, 1676, 1604, 1495 cm$^{-1}$

NMR (CDCl$_3$, δ): 0.93 (3H, t, J=6Hz), 1.20–1.60 (5H, m), 1.75–2.05 (2H, m), 2.22 (1H, m), 2.43 (1H, m), 2.80–3.05 (2H, m), 5.40 (2H, s), 7.16 (2H, s), 7.54 (1H, t, J=8Hz), 7.62–7.88 (4H, m), 8.09 (1H, d, J=8Hz), 8.19 (1H, d, J=8Hz)

EXAMPLE 19

2,2-Dibutyl-3,4-dihydro-7-(2-quinolylmethoxy)-1(2H)-naphthalenone mp: 88°–89° C.

IR (CHCl$_3$): 2950, 2925, 1676, 1603, 1495 cm$^{-1}$

NMR (CDCl$_3$, δ): 0.88 (6H, t, J=8Hz), 1.10–1.80 (12H, m), 2.01 (2H, t, J=6Hz), 2.90 (2H, t, J=6Hz), 5.40 (2H, s), 7.15 (2H, s), 7.50–7.89 (5H, m), 8.10 (1H, d, J=8Hz), 8.21 (1H, dd, J=2, 8Hz)

Following compound was prepared according to a similar manner to that of Example 6.

EXAMPLE 20

2-Butyl-5-(2-quinolylmethoxy)-1,2,3,4-tetrahydro-1-naphthol mp: 130°–133° C.

IR (CHCl$_3$): 3350, 2925, 1599, 1581 cm$^{-1}$

NMR (CDCl$_3$, δ): 0.88–1.02 (3H, m), 1.20–2.20 (10H, m), 2.53–3.18 (2H, m), 4.45 (0.5H, t, J=6Hz), 4.66 (0.5H, d, J=5Hz), 5.38 (2H, s), 6.80–7.24 (3H, m), 7.55 (1H, t, J=8Hz), 7.69 (1H, d, J=8Hz), 7.75 (1H, t, J=8Hz), 7.84 (1H, d, J=8Hz), 8.08 (1H, d, J=8Hz), 8.20 (1H, d, J=8Hz)

EXAMPLE 21

To a stirring solution of 2-butyl-3,4-dihydro-7-(2-quinolylmethoxy)-1(2H)-naphthalenone (718 mg) in methanol (7 ml) in an ice bath was added dropwise a solution of sodium borohydride (114 mg) in methanol (7 ml). The mixture was stirred for half an hour at the same temperature and then diluted with chloroform (80 ml). The solution was washed with water (80 ml). The aqueous layer was extracted three times with chloroform. The combined organic layers were washed with water, dried and concentrated in vacuo to give an oily residue. The residue was dissolved in ether (200 ml) and thereto 2N-hydrogen chloride in ethyl acetate (1 ml) was added dropwise with stirring in an ice bath. The precipitates were collected by filtration and washed with ether to yield 2-butyl-7-(2-quinolylmethoxy)-1,2,3,4-tetrahydro-1-naphthol hydrochloride (700 mg).

mp: 128°–131° C.

IR (Nujol): 3220, 1607, 1598, 1501 cm$^{-1}$

NMR (CD$_3$OD, δ): 0.80–1.05 (3H, m), 1.10–2.17 (9H, m), 2.60–2.84 (2H, m), 4.30 (0.5H, d, J=7Hz), 4.58 (0.5H, s), 5.70 (2H, s), 6.94–7.17 (2H, m), 7.25 (1H, d, J=2Hz), 7.99 (1H, t, J=8Hz), 8.18 (1H, d, J=8Hz), 8.20 (1H, t, J=8Hz), 8.32–8.43 (2H, m), 9.16 (1H, d, J=8Hz)

EXAMPLE 22

2,2-Dibutyl-7-(2-quinolylmethoxy)-1,2,3,4-tetrahydro-1-naphthol hydrochloride was prepared according to a similar manner to that of Example 21.

mp: 172°–174° C.

IR (Nujol): 3340, 1501, 1499 cm$^{-1}$
NMR (CD$_3$OD, δ): 0.83–1.02 (6H, m), 1.10–1.87 (14H, m), 2.62–2.75 (2H, m), 4.27 (1H, s), 5.69 (2H, s), 6.98–7.18 (3H, m), 7.98 (1H, t, J=8Hz), 8.17 (1H, d, J=8Hz), 8.19 (1H, t, J=8Hz), 8.34 (1H, d, J=8Hz), 8.38 (1H, d, J=8Hz), 9.15 (1H, d, J=8Hz)

Following compounds were prepared according to a similar manner to that of Example 5.

EXAMPLE 23

2-Butyl-3,4-dihydro-7-(2-quinolylmethoxy)-1(2H)-naphthalenone hydrochloride mp: 152°–153° C.
IR (Nujol): 3440, 1675, 1602 cm$^{-1}$
NMR (CDCl$_3$, δ): 0.93 (3H, t, J=6Hz), 1.20–1.60 (7H, m), 2.27 (1H, m), 2.50 (1H, m), 2.93–3.03 (2H, m), 5.75 (2H, s), 7.30–7.47 (2H, m), 7.67 (1H, d, J=2Hz), 7.99 (1H, t, J=8Hz), 8.19 (1H, d, J=8Hz), 8.21 (1H, t, J=8Hz), 8.35 (1H, d, J=8Hz), 8.39 (1H, d, J=8Hz), 9.18 (1H, d, J=8Hz)

EXAMPLE 24

2,2-Dibutyl-3,4-dihydro-7-(2-quinolylmethoxy)-1(2H)-naphthalenone hydrochloride mp: 170°–173° C.
IR (Nujol): 1665, 1601, 1497 cm$^{-1}$
NMR (CD$_3$OD, δ): 0.89 (6H, t, J=7Hz), 1.10–1.80 (12H, m), 2.05 (2H, t, J=6Hz), 2.97 (2H, t, J=6Hz), 5.76 (2H, s), 7.33 (1H, d, J=8Hz), 7.39 (1H, dd, J=2, 8Hz), 7.68 (1H, d, J=2Hz), 8.00 (1H, t, J=8Hz), 8.10–8.43 (4H, m), 9.19 (1H, d, J=8Hz)

EXAMPLE 25

2,2-Dibutyl-3,4-dihydro-5-(2-quinolylmethoxy)-(1(2H)-naphthalenone hydrochloride mp: 118°–119° C.
NMR (CDCl$_3$, δ): 0.89 (6H, t, J=6Hz), 1.10–1.80 (12H, m), 2.08 (2H, t, J=6Hz), 3.02 (2H, t, J=6Hz), 5.99 (2H, s), 7.18–7.38 (2H, m), 7.75 (1H, d, J=8Hz), 7.89 (1H, t, J=8Hz), 8.03–8.20 (3H, m), 8.82 (1H, d, J=8Hz), 8.94 (1H, d, J=8Hz)

Preparation 16

2,2-Dibutyl-3,4-dihydro-5-hydroxy-8-methyl-1(2H)-naphthalenone was prepared according to a similar manner to that of Preparation 2.

mp: 77.5°–78.0° C.
IR (CHCl$_3$): 3600, 3330, 2960, 2950, 2870, 1675, 1585, 1275 cm$^{-1}$
NMR (CDCl$_3$, δ): 0.88 (6H, t, J=6Hz), 1.00–1.40 (8H, m), 1.50–1.65 (4H, m), 2.01 (2H, t, J=7Hz), 2.51 (3H, s), 2.81 (2H, t, J=7Hz), 5.18 (1H, s), 6.83 (1H, d, J=8Hz), 6.98 (1H, d, J=8Hz)

Preparation 17

2,2-Dibutyl-3,4-dihydro-5-methoxy-8-methyl-1(2H)-naphthalenone was prepared according to a similar manner to that of Preparation 1.

oil
IR (CHCl$_3$): 2960, 2940, 2860, 1675, 1580, 1470, 1260, 1240, 1210 cm$^{-1}$
NMR (CDCl$_3$, δ): 0.88 (6H, t, J=6Hz), 1.00–1.45 (8H, m), 1.45–1.70 4H, m), 1.97 (2H, t, J=7Hz), 2.53 (3H, s), 2.86 (2H, t, J=7Hz), 3.83 (3H, s), 6.88 (1H, d, J=8Hz), 7.05 (1H, d, J=8Hz)

Preparation 18

2,2-Dibutyl-3,4-dihydro-5,8-dihydroxy-1(2H)-naphthalenone was prepared according to a similar manner to that of Preparation 2.

oil
IR (CHCl$_3$): 3600, 3330, 2940, 2870, 1632, 1585, 1465, 1280, 1265, 1185, 1150 cm$^{-1}$
NMR (CDCl$_3$, δ): 0.90 (6H, t, J=6Hz), 1.10–1.42 (8H, m), 1.42–1.80 (4H, m), 2.02 (2H, t, J=7Hz), 2.84 (2H, t, J=7Hz), 4.44 (1H, br s), 6.72 (1H, d, J=8Hz), 6.97 (1H, d, J=8Hz), 12.36 (1H, s)

Preparation 19

2,2-Dibutyl-3,4-dihydro-5,8-dimethoxy-1(2H)-naphthalenone was prepared according to a similar manner to that of Preparation 1.

oil
IR (CHCl$_3$): 2930, 2850, 1672, 1585, 1462, 1433, 1255, 1200, 1080, 970 cm$^{-1}$
NMR (CDCl$_3$, δ): 0.88 (6H, t, J=6Hz), 1.05–1.40 (8H, m), 1 45–1.60 (4H, m), 1.94 (2H, t, J=7Hz), 2.83 (2H, t, J=7Hz), 3.81 (3H, s), 3.84 (3H, s), 6.79 (1H, d, J=8Hz), 6.93 (1H, d, J=8Hz)

Preparation 20

8-Chloro-2,2-dibutyl-3,4-dihydro-5-hydroxy-1(2H)-naphthalenone was prepared according to a similar manner to that of Preparation 2.

oil
IR (CHCl$_3$): 3300, 2930, 2850, 1685, 1575, 1450, 1280 cm$^{-1}$
NMR (CDCl$_3$, δ): 0.88 (6H, t, J=6Hz), 1.05–1.40 (8H, m), 1.50–1.75 (4H, m), 2.02 (2H, t, J=7Hz), 2.86 (2H, t, J=7Hz), 5.36 (1H, s), 6.86 (1H, d, J=8Hz), 7.18 (1H, d, J=8Hz)

Preparation 21

8-Chloro-2,2-dibutyl-3,4-dihydro-5-methoxy-1(2H)-naphthalenone was prepared according to a similar manner to that of Preparation 1.

oil
IR (CHCl$_3$): 2930, 2850, 1685, 1575, 1455, 1435, 1255, 1200 cm$^{-1}$
NMR (CDCl$_3$, δ): 0.88 (6H, t, J=6Hz), 1.05–1.40 (8H, m), 1.50–1.70 (4H, m), 1.98 (2H, t, J=7Hz), 2.84 (2H, t, J=7Hz), 3.85 (3H, s), 6.86 (1H, d, J=8Hz), 7.26 (1H, d, J=8Hz)

Preparation 22

3,4-Dihydro-2,2-diisobutyl-5-hydroxy-1(2H)-naphthalenone was prepared according to a similar manner to that of Preparation 2.

oil
IR (CHCl$_3$): 3320, 2950, 2860, 1670, 1600, 1585, 1460, 1270, 1150, 1070, 895 cm$^{-1}$
NMR (CDCl$_3$, δ): 0.83 (6H, d, J=6Hz), 0.89 (6H, d, J=6Hz), 1 35–1.85 (6H, m), 2.10 (2H, t, J=6Hz), 2.90 (2H, t, J=6Hz), 5.35 (1H, br s), 6.97 (1H, d, J=8Hz), 7.18 (1H, t, J=8Hz), 7.63 (1H, d, J=8Hz)

Preparation 23

3,4-Dihydro-2,2-diisobutyl-5-methoxy-1(2H)-naphthalenone was prepared according to a similar manner to that of Preparation 1.

oil
IR (CHCl$_3$): 2940, 2860, 1670, 1590, 1580, 1460, 1435, 1310, 1250, 1210, 1045 cm$^{-1}$ NMR (CDCl$_3$, δ): 0.83 (6H, d, J=6Hz), 0.88 (6H, d, J=6Hz), 1.35–1.80 (6H, m), 2.05 (2H, t, J=6Hz), 2.89 (2H, t, J=6Hz), 3.86 (3H, s), 6.99 (1H, d, J=8Hz), 7.26 (1H, t, J=8Hz), 7.64 (1H, d, J=8Hz)

Preparation 24

2,2-Dibutyl-3,4-dihydro-8-fluoro-5-methoxy-1(2H)-naphthalenone was prepared according to a similar manner to that of Preparation 1.

oil

IR (neat): 2940, 2850, 1680, 1600, 1580, 1460, 1250 cm$^{-1}$

NMR (CDCl$_3$, δ): 0.85 (6H, t, J=7Hz), 1.14–1.33 (8H, m), 1.53–1.64 (4H, m), 1.98 (2H, t, J=7Hz), 2.87 (2H, t, J=7Hz), 3.85 (3H, s), 6.92–6.95 (2H, m)

Preparation 25

2,2-Dibutyl-3,4-dihydro-8-fluoro-5-hydroxy-1(2H)-naphthalenone was prepared according to a similar manner to that of Preparation 2.

mp: 99°–101° C.

IR (Nujol): 3360, 1670, 1610, 1580, 1375, 1290, 1240 cm$^{-1}$

NMR (CDCl$_3$, δ): 0.88 (6H, t, J=7Hz), 1.18–1.33 (8H, m), 1.55–1.63 (4H, m), 2.05 (2H, t J=7Hz), 2.85 (2H, t, J=7Hz), 5.30 (1H, s), 6.80–7.00 (2H, m)

The following compounds were prepared according to a similar manner to that of Example 1.

EXAMPLE 26

2,2-Dibutyl-5-[2-(1-methylbenzimidazolyl)methoxy]-1,2,3,4-tetrahydro-1-naphthol mp: 201°–203° C.

IR (CHCl$_3$): 3600, 3300, 2950, 2930, 2860, 1585, 1465, 1455, 1250, 1085, 1070 cm$^{-1}$

NMR (CDCl$_3$, δ): 0.87 (3H, t, J=6Hz), 0.93 (3H, t, J=6Hz), 1.00–1.80 (15H, m), 2.47 (1H, m), 2.73 (1H, m), 3.90 (3H, s), 4.33 (1H, br s), 5.38 (2H, s), 7.00–7.10 (2H, m), 7.15–7.45 (4H, m), 7.79 (1H, m)

EXAMPLE 27

2,2-Dibutyl-5-[2-(3-methyl-1,4-naphthalenedionyl)methoxy]-1,2,3,4-tetrahydro-1-naphthol oil IR (CHCl$_3$): 3600, 3300, 2950, 2920, 2850, 1660, 1625, 1595. 1580, 1460, 1295. 1250 cm$^{-1}$ NMR (CDCl$_3$, δ): 0.87 (3H, t, J=6Hz), 0.96 (3H, t, J=6Hz), 1.00–1.80 (15H, m), 2.35 (3H, s), 2.43 (1H, m), 2.68 (1H, m), 4.33 (1H, s), 5.10 (1H, d, J=11Hz), 5.18 (1H, d, J=11Hz), 6.29 (1H, d, J=8Hz), 7.03 (1H, d, J=8Hz), 7.21 (1H, t, J=8Hz), 7.65–7.85 (2H, m), 8.05–8.25 (2H, m)

EXAMPLE 28

2,2-Dibutyl-3,4-dihydro-8-methyl-5-(2-quinolylmethoxy)-1(2H)-naphthalenone mp: 68.0°–69.0° C.

IR (CHCl$_3$): 2960, 2940, 2860, 1675, 1580, 1470, 1455, 1260, 1205 cm$^{-1}$

NMR (CDCl$_3$, δ): 0.90 (6H, t, J=6Hz), 1.05–1.40 (8H, m), 1.50–1.70 (4H, m), 2.02 (2H, t, J=7Hz), 2.51 (3H, s), 3.03 (2H, t, J=7Hz), 5.39 (2H, s), 6.94 (1H, d, J=8Hz), 7.01 (1H, d, J=8Hz), 7.57 (1H, t, J=8Hz), 7.63–7.90 (3H, m), 8.10 (1H, d, J=8Hz), 8.22 (1H, d, J=8Hz)

EXAMPLE 29

2,2-Dibutyl-3,4-dihydro-8-hydroxy-5-(2-quinolylmethoxy)-1(2H)-naphthalenone oil

IR (CHCl$_3$): 3270, 2930, 2860, 1635, 1605, 1580, 1465, 1260, 1185, 1095, 1060, 820 cm$^{-1}$

NMR (CDCl$_3$, δ): 0.90 (6H, t, J=6Hz), 1.10–1.42 (8H, m), 1.42–1.82 (4H, m), 2.01 (2H, t, J=7Hz), 3.00 (2H, t, J=7Hz), 5.34 (2H, s), 6.75 (1H, d, J=8Hz), 7.12 (1H, d, J=8Hz), 7.57 (1H, t, J=8Hz), 7.62–7.90 (3H, m), 8.09 (1H, d, J=8Hz), 8.22 (1H, d, J=8Hz), 12.29 (1H, s)

EXAMPLE 30

8-Chloro-2,2-dibutyl-3,4-dihydro-5-(2-quinolylmethoxy)-1(2H)-naphthalenone oil

IR (CHCl$_3$): 2930, 2850, 1685, 1570, 1445, 1250, 1205 cm$^{-1}$

NMR (CDCl$_3$, δ): 0.88 (6H, t, J=6Hz), 1.05–1.40 (8H, m), 1.50–1.75 (4H, m), 2.02 (2H, t, J=7Hz), 3.01 (2H, t, J=7Hz), 5.40 (2H, s), 6.96 (1H, d, J=8Hz), 7.22 (1H, d, J=8Hz), 7.57 (1H, t, J=8Hz), 7.63 (1H, d, J=8Hz), 7.77 (1H, t, J=8Hz), 7.85 (1H, d, J=8Hz), 8.09 (1H, t, J=8Hz), 8.22 (1H, d, J=8Hz)

EXAMPLE 31

3,4-Dihydro-2,2-diisobutyl-5-(2-quinolylmethoxy)-1(2H)-naphthalenone oil

IR (CHCl$_3$): 2950, 2860, 1675, 1595, 1580, 1465, 1450, 1250, 1205 cm$^{-1}$

NMR (CDCl$_3$, δ): 0.84 (6H, d, J=6Hz), 0.91 (6H, d, J=6Hz), 1.40–1 85 (6H, m), 2.11 (2H, t, J=6Hz), 3.06 (2H, t, J=6Hz), 5.43 (2H, s), 7.10 (1H, d, J=8Hz), 7.23 (1H, d, J=8Hz), 7.57 (1H, t, J=8Hz), 7.62–7.80 (3H, m), 7.86 (1H, d, J=8Hz), 8 10 (1H, d, J=8Hz), 8.24 (1H, d, J=8Hz)

EXAMPLE 32

2,2-Dibutyl-3,4-dihydro-8-fluoro-5-(2-quinolylmethoxy)-1(2H)-naphthalenone mp: 74°–76° C.

IR (Nujol): 1690, 1610, 1580, 1250, 1220, 820 cm$^{-1}$

NMR (CDCl$_3$, δ): 0.92 (6H, t, J=7Hz), 1.15–1.38 (8H, m), 1.56–1.66 (4H, m), 2.03 (2H, t, J=7Hz), 3.02 (2H, t, J=7Hz), 5.37 (2H, s), 6.87–7.08 (2H, m), 7.54–7.89 (4H, m), 8.10 (1H, d, J=10Hz), 8.23 (1H, d, J=10Hz)

EXAMPLE 33

To a solution of 8-chloro-2,2-dibutyl-3,4-dihydro-5-(2-quinolylmethoxy)-1(2H)-naphthalenone (180 mg) in freshly distilled tetrahydrofuran (5 ml) was added lithium aluminum hydride (15 mg) with stirring in an ice bath under nitrogen and the mixture was stirred for 15 minutes in an ice bath. To the mixture was carefully added aqueous saturated ammonium chloride solution (5 ml) in an ice bath, and then diethylether (10 ml) was added thereto The separated aqueous layer was extracted two times with diethyl ether and the combined organic layers were washed with brine. The organic layer was dried over magnesium sulfate and concentrated in vacuo to give the oily residue which was crystallized from diisopropyl ether to yield 8-chloro-2,2- dibutyl-5-(2-quinolylmethoxy)-1,2,3,4-tetrahydro-1-naphthol (142 mg).

mp: 142.5°–143.5° C.

IR (CHCl₃): 3600, 3330, 2930, 2860, 1620, 1600, 1580, 1505, 1460, 1290, 1250, 1205, 1090, 820 cm⁻¹

NMR (CDCl₃, δ): 0.88 (3H, t, J=6Hz), 0.98 (3H, t, J=6Hz), 1.05-2.05 (15H, m), 2.40-2.70 (1H, m), 2.98 (1H, dd, J=18, 6Hz), 4.61 (1H, s), 5.37 (2H, s), 6.79 (1H, d, J=8Hz), 7.18 (1H, d, J=8Hz), 7.57 (1H, t, J=8Hz), 7.66 (1H, d, J=8Hz), 7.75 (1H, t, J=8Hz), 7.85 (1H, d, J=8Hz), 8.08 (1H, d, J=8Hz), 8.21 (1H, d, J=8Hz)

EXAMPLE 34

2,2-Dibutyl-8-fluoro-5-(2-quinolylmethoxy)-1,2,3,4-tetrahydro-1-naphthol was prepared according to a similar manner to that of Example 33.

mp: 128°–129° C.

IR (Nujol): 3300, 1600, 1240, 1220, 1080, 1030 cm⁻¹

NMR (CDCl₃, δ): 0.85-1.79 (21H, m), 2.45-2.61 (1H, m), 3.00 (1H, dd, J=19, 5Hz), 4.64 (1H, d, J=5Hz), 5.37 (2H, s), 6.72-6.93 (2H, m), 7.57 (1H, t, J=8Hz), 7.63-7.87 (3H, m), 8.10 (1H, d, J=8Hz), 8.22 (1H, d, J=8Hz)

EXAMPLE 35

2,2-Dibutyl-8-methyl-5-(2-quinolylmethoxy)-1,2,3,4-tetrahydro-1-naphthol was prepared according to a similar manner to that of Example 33.

mp: 149°–151° C.

IR (CHCl₃): 3610, 3350, 2960, 2940, 2860, 1620, 1600, 1590, 1480, 1260, 1095, 825 cm⁻¹

NMR (CDCl₃, δ): 0.88 (3H, t, J=6Hz), 0.98 (3H, t, J=6Hz), 1.04-1.80 (15H, m), 2.39 (3H, s), 2.43-2.70 (1H, m), 3.00 (1H, dd, J=18, 6Hz), 4.40 (1H, d, J=5Hz), 5.37 (2H, s), 6.77 (1H, d, J=8Hz), 6.98 (1H, d, J=8Hz), 7.58 (1H, d, J=8Hz), 7.65-7.90 (3H, m), 8.09 (1H, d, J=8Hz), 8.22 (1H, d, J=8Hz)

EXAMPLE 36

2,2-Dibutyl-8-hydroxy-5-(2-quinolylmethoxy)-1,2,3,4-tetrahydro-1-naphthol hydrochloride was prepared according to a similar manner to that of Example 6.

mp: 148°–152° C.

IR (Nujol): 3450, 3100, 2920, 2850, 2720, 2670, 1645, 1603, 1260, 1230 cm⁻¹

NMR (CDCl₃:CD₃OD=1:1, δ): 0.85 (3H, t, J=6Hz), 0.90 (3H, t, J=6Hz), 1.05-1.90 (15H, m), 2.57 (1H, m), 2.88 (1H, m), 4.67 (1H, s), 5.72 (2H, s), 6.67 (1H, d, J=8Hz), 6.82 (1H, d, J=8Hz), 7.97 (1H, t, J=8Hz), 8.10-8.35 (3H, m), 8.61 (1H, d, J=8Hz), 9.03 (1H, d, J=8Hz)

EXAMPLE 37

2,2-Diisobutyl-5-(2-quinolylmethoxy)-1,2,3,4-tetrahydro-1-naphthol was prepared according to a similar manner to that of Example 6.

mp: 144.5°–145.5° C.

IR (CHCl₃): 3330, 2950, 2860, 1600, 1585, 1465, 1260, 1250, 1200, 1090, 820 cm⁻¹

NMR (CDCl₃, δ): 0.90 (3H, d, J=6Hz), 0.98 (3H, d, J=6Hz), 1.03 (3H, d, J=6Hz), 1.06 (3H, d, J=6Hz), 1.18-2.00 (9H, m), 2.60-3.00 (2H, m), 4.43 (1H, br s), 5.39 (2H, s), 6.84 (1H, d, J=8Hz), 7.00 (1H, d, J=8Hz), 7.15 (1H, t, J=8Hz), 7.55 (1H, t, J=8Hz), 7.70 (1H, d, J=8Hz), 7.74 (1H, t, J=8Hz), 7.83 (1H, d, J=8Hz), 8.08 (1H, d, J=8Hz), 8.20 (1H, d, J=8Hz)

EXAMPLE 38

2,2-Dibutyl-3,4-dihydro-8-hydroxy-5-(2-quinolylmethoxy)-1(2H)-naphthalenone hydrochloride was prepared according to a similar manner to that of Example 5.

mp: 135°–145° C. (dec.)

IR (Nujol): 3530, 2950, 2930, 2850, 1640, 1610, 1465, 1380, 1265, 1245, 1190 cm⁻¹

NMR (CDCl₁, δ): 0.90 (6H, t, J=6Hz), 1.05-1.42 (8H, m), 1.45-1.85 (4H, m), 2.07 (2H, t, J=7Hz), 3.00 (2H, t, J=7Hz), 5.95 (2H, s), 6.79 (1H, d, J=8Hz), 7.24 (1H, d, J=8Hz), 7.92 (1H, t, J=8Hz), 8.05-8.25 (3H, m), 8.88 (1H, d, J=8Hz), 8.99 (1H, d, J=8Hz), 12.37 (1H, s)

EXAMPLE 39

2,2-Dibutyl-3,4-dihydro-8-methyl-5-(2-quinolylmethoxy)-1(2H)-naphthalenone hydrochloride was prepared according to a similar manner to that of Example 5.

mp: 162°–164° C. (dec.)

IR (CHCl₃): 3400, 2960, 2940, 2300, 1960, 1675, 1645, 1600, 1580, 1255, 1240, 1205, 1100 cm⁻¹

NMR (CDCl₃, δ): 0.90 (6H, t, J=6Hz), 1.05-1.45 (8H, m), 1.50-1.70 (4H, m), 2.05 (2H, t, J=7Hz), 2.52 3H, s), 3 04 2H, t, J=7Hz), 6.01 (2H, s), 7.00-7.20 (2H, m), 7.93 (1H, t, J=8Hz), 8.00-8.25 3H, m), 8.91 (1H, d, J=8Hz), 9.02 (1H, d, J=8Hz)

Preparation 26

To a suspension of Lithium aluminium hydride (2.08 g) in freshly distilled tetrahydrofuran (27.50 ml) was added dropwise a solution of (S)-(-)-4-anilino-3-methylamino-1-butanol (11.05 g) in freshly distilled tetrahydrofuran (27.50 ml) during a period of one and half hours in an ice bath under nitrogen. The suspension was stirred for one hour at ambient temperature and then allowed to cool to −63° C. To the suspension was added dropwise a solution of 2,2-dibutyl-5-hydroxy-1(2H)-naphthalenone (3.00 g) in freshly distilled tetrahydrofuran (27.50 ml) during a period of half an hour at the same temperature. The mixture was stirred for 4 hours at −62° to −65° C. and allowed to warm to 0° C. To the mixture was carefully added aqueous saturated ammonium chloride solution (35 ml), maintaining the reaction temperature below 10° C. in an ice bath.

The aqueous layer was extracted three times with ethyl acetate. The combined organic layers were washed with aqueous 1N sulfuric acid solution, brine, aqueous saturated sodium hydrogen carbonate solution, and brine. The organic layer was dried over magnesium sulfate and concentrated in vacuo to give an amorphous solid which was crystallized from hexane to yield (+)-2,2-dibutyl-5-hydroxy-1,2,3,4-tetrahydro-1-naphtol as white solid.

mp: 84°–87° C.

IR (Nujol): 3500, 1580, 1370, 1150, 1080 cm⁻¹

NMR (CDCl₃, δ): 0.87-0.95 (m, 6H), 1.21-1.84 (m, 15H), 2.38-2.76 (m, 2H), 4.34 (s, 1H), 4.92 (s, 1H), 6.70 (d, 1H, J=9Hz), 6.95-7.15 (m, 2H).

|  | C | H |
|---|---|---|
| Calc. | 78.21 | 10.21 |
| Found | 78.12 | 10.27 |

EXAMPLE 40

To a suspension of lithium aluminum hydride (3.80 g) in freshly distilled tetrahydrofuran (120 ml) was added dropwise a solution of (S)-(−)-4-anilino-3-methylamino-10 butanol (19.96 g) in freshly distilled tetrahydrofuran (60 ml) during a period of one and half hours in an ice bath under nitrogen. The suspension was stirred for one hour at ambient temperature and then allowed to cool to −63° C. To the suspension was added dropwise a solution of 2,2-dibutyl-3,4-dihydro-5-(2-quinolylmethoxy)-1(2H)-naphthalenone (13.84 g) in freshly distilled tetrahydrofuran (60 ml) during a period of half hour at the same temperature. The mixture was stirred for 2 hours at −61 to −63° C. and allowed to warm to 0° C. To the mixture was carefully added aqueous saturated ammonium chloride solution (250 ml), maintaining the reaction temperature below 12° C. in an ice bath, and then diethylether (100 ml) was added thereto.

The separated aqueous layer was extracted three times with diethylether. The combined organic layers were washed with aqueous 1N citric acid solution, brine, aqueous sodium bicarbonate solution, and brine. The organic layer was dried over magnesium sulfate and concentrated in vacuo to give an amorphous solid which was crystallized from methanol to yield (+)-2,2-dibutyl-5-(2-quinolylmethoxy)-1,2,3,4-tetrahydro-1-naphthol (13.81 g) as white solid.

mp: 62°–65° C.
$[\alpha]_D^{20}$ +10.33°(c=0.59, MeOH)

EXAMPLE 41

To a solution of (+)-2,2-dibutyl-5-(2-quinolylmethoxy)-1,2,3,4-tetrahydro-1-naphthol (14.5 g) in ethyl acetate (145 ml) was added 3N-hydrogen chloride solution in ethyl acetate (20 ml) in one portion with vigorous stirring at ambient temperature. After stirring for 20 minutes, the precipitates were collected by filtration and washed with ethyl acetate. The pale yellow solid was recrystallized from acetonitrile to yield (+)-2,2-dibutyl-5-(2-quinolylmethoxy)-1,2,3,4-tetrahydro-1-naphthol hydrochloride (11.605 g) as white solid.

mp: 138°–140° C.
$[\alpha]_D^{25}$ +6.9°(c=0.62, MeOH)
NMR (CD$_3$OD, δ): 0.88 (3H, t, J=6Hz), 0.96 (3H, t, J=6Hz), 1.10–1.90 (14H, m), 2.63 (1H, m), 2.91 (1H, m), 4.30 (1H, s), 5.71 (2H, s), 6.98 (1H, d, J=8Hz), 7.08 (1H, d, J=8Hz), 7.22 (1H, t, J=8Hz), 8.00 (1H, t, J=8Hz), 8.16–8.43 (4H, m), 9.22 (1H, d, J=8Hz)

EXAMPLE 42

A solution of borane in tetrahydrofuran (1.0 M solution in THF, 76 ml) was added dropwise for 20 minutes to a solution of S-(−)-2-amino-1,1-diphenyl-3-methylbutan-1-ol (7.65 g) in freshly distilled tetrahydrofuran (50 ml) at −65° C. under nitrogen. After addition, the resulting mixture was gradually warmed to 4° C. and stirred for 6 hours at 4°–6° C. To the solution was added dropwise a solution of 2,2-dibutyl-3,4-dihydro-5-(2-quinolylmethoxy)-1(2H)-naphthalenone (4.98 g) in freshly distilled tetrahydrofuran (40 ml) during a period of half hour at 4°–6° C. and then stirred overnight at ambient temperature. To the mixture was added aqueous 2N hydrochloric acid (20 ml) at 4°–10° C. The mixture was stirred for one and half hours at ambient temperature completely to decompose the reducing reagent and aqueous 4N sodium hydroxide solution was added in one portion. The separated oil was extracted with diethyl ether (x2). The extracts were washed with aqueous 1N citric acid (x3), brine, aqueous sodium bicarbonate solution and brine successively. The dried solvent was evaporated to give the oily residue (7.71 g) which was purified by crystallization with n-hexane and then methanol. The obtained crystals were dissolved in ethyl acetate and treated with hydrogen chloride to yield (+)-2,2-dibutyl-5-(2-quinolylmethoxy)-1,2,3,4-tetrahydro-1-naphthol hydrochloride (2.82 g) as white solid.

This object compound was confirmed to be the same compound as one prepared in Example 41 by comparing both physical constants.

The following compounds were prepared according to a similar manner to that of Example 40.

EXAMPLE 43

(+)-8-Chloro-2,2-dibutyl-5-(2-quinolylmethoxy)-1,2,3,4-tetrahydro-1-naphthol.

mp: 94.5°–95.5° C.
$[\alpha]_D^{20}$ = +17.9°(c=1.018 CHCl$_3$)
IR (CHCl$_3$): 3600, 3330, 2960, 2940, 2860, 1620, 1600, 1580, 1510, 1470, 1295, 1255, 1095, 825 cm$^{-1}$
NMR (CDCl$_3$, δ): 0.88 (3H, t, J=6Hz), 0.98 (3H, t, J=6Hz), 1.05–2.05 (15H, m), 2.40–2.70 (1H, m), 2.98 (1H, dd, J=18Hz, 6Hz), 4.61 (1H, s), 5.36 (2H, s), 6.79 (1H, d, J=8Hz), 7.18 (1H, d, J=8Hz), 7.57 (1H, t, J=8Hz), 7.66 (1H, d, J=8Hz), 7.75 (1H, t, J=8Hz), 7.85 (1H, d, J=8Hz), 8.08 (1H, d, J=8Hz), 8.21 (1H, d, J=8Hz).

EXAMPLE 44

(+)-2,2-Dibutyl-8-methyl-5-(2-quinolylmethoxy)-1,2,3,4-tetrahydro-1-naphthol.

mp: 84.5°–86.0° C.
$[\alpha]_D^{20}$ = +29.5° (c=1.003, CHCl$_3$)
IR (CHCl$_3$): 3600, 3350, 2960, 2940, 2860, 1620, 1600, 1590, 1480, 1260, 1095, 825 cm$^{-1}$
NMR (CDCl$_3$, δ): 0.88 (3H, t, J=6Hz), 0.98 (3H, t, J=6Hz), 1.04–1.80 (15H, m), 2.39 (3H, s), 2.43–2.70 (1H, m), 3.00 (1H, dd, J=18Hz, 6Hz), 4.40 (1H, s(br.), 5.37 (2H, s), 6.77 (1H, d, J=8Hz), 6.98 (1H, d, J=8Hz), 7.58 (1H, d, J=8Hz), 7.65–7.90 (3H, m), 8.09 (1H, d, J=8Hz), 8.22 (1H, d, J=8Hz).

EXAMPLE 45

(+)-5-(2-Carbamoylbenzyloxy)-2,2-dibutyl-1,2,3,4-tetrahydro-1-naphthol mp: 65°–70° C.
IR (Nujol): 3350, 3170, 1660, 1580, 1375 cm$^{-1}$
NMR (CDCl$_3$, δ): 0.87 (3H, t, J=7Hz), 0.95 (3H, t, J=7Hz), 1.11–1.43 (10H, m), 1.50–1.78 (5H, m), 2.40–2.57 (1H, m), 2.70–2.84 (1H, m), 4.32 (1H, s), 5.28 (2H, s), 5.87 (1H, bs), 6.40 (1H, bs), 6.89 (1H, d, J=8Hz), 7.02 (1H, d, J=8Hz), 7.17 (1H, d, J=8Hz), 7.42 (1H, d, J=8Hz), 7.52 (1H, t, J=8Hz), 7.64 (2H, t, J=8Hz)
$[\alpha]_D^{21}$ = +11.9° (c=0.50, CHCl$_3$)

EXAMPLE 46

(+)-2,2-Diisobutyl-5-(2-quinolylmethoxy)-1,2,3,4-tetrahydro-1-naphthol mp: 70°–71° C.
IR (Nujol): 3400, 1600, 1585, 1370, 1260, 1100 cm$^{-1}$
NMR (CDCl$_3$, δ): 0.83–1.97 (21H, m), 2.63–3.00 (2H, m), 4.43 (1H, d, J=4Hz), 5.40 (2H, s), 6.84 (1H, d, J=8Hz), 7.02 (1H, d, J=8Hz), 7.18 (1H, t, J=8Hz), 7.57 (1H, t, J=8Hz), 7.68-7.88 (3H, m), 8.10 (1H, d, J=9Hz), 8.22 (1H, d, J=9Hz)

$[\alpha]_D^{22} = +24.5°$ (c=1.00, CHCl$_3$)

EXAMPLE 47

(+)-2,2-Dibutyl-8-fluoro-5-(2-quinolylmethoxy)-1,2,3,4-tetrahydro-1-naphthol mp: 122°-124° C.

IR (Nujol): 3350, 1620, 1600, 1510, 1260, 1240, 1100 cm$^{-1}$

NMR (CDCl$_3$, δ): 0.87-1.80 (21H, m), 2.47-2.65 (1H, m), 2.99 (1H, dd, J=19Hz; 5Hz), 4.62 (1H, d, J=5Hz), 5.35 (2H, s), 6.75-6.90 (2H, m), 7.57 (1H, t, J=8Hz), 7.68 (1H, d, J=8Hz), 7.72-7.87 (2H, m), 8.10 (1H, d, J=8Hz), 8.22 (1H, d, J=8Hz)

$[\alpha]_D^{20} = +6.9°$ (c=1.00, CHCl$_3$)

The following compounds were prepared according to a similar manner to that of Example 1.

EXAMPLE 48

(+)-5-(2-Benzothiazolylmethoxy)-2,2-dibutyl-1,2,3,4-tetrahydro-1-naphthol mp: 107.0°-107.5° C.

$[\alpha]_D^{20} = +9.8°$ (c=1.046, CHCl$_3$)

IR (CHCl$_3$): 3600, 3450, 2960, 2940, 2860, 1585, 1470, 1260, 1095 cm$^{-1}$

NMR (CDCl$_3$, δ): 0.88 (3H, t, J=6Hz), 0.95 (3H, t, J=6Hz), 1.08-1.86 (15H, m), 2.60 (1H, m), 2.90 (1H, m), 4.35 (1H, s), 5.48 (2H, s), 6.86 (1H, d, J=8Hz), 7.06 (1H, d, J=8Hz), 7.20 (1H, t, J=8Hz), 7.41 (1H, d, J=8Hz), 7.51 (1H, t, J=8Hz), 7.91 (1H, d, J=8Hz), 8.03 (1H, d, J=8Hz)

EXAMPLE 49

5-(2-Cyanobenzyloxy)-2,2-dibutyl-3,4-dihydro-1(2H)-naphthalenone.

IR (Nujol): 2220, 1670, 1595, 1580, 1375, 1340, 1305, 1170, 1080, 1040 cm$^{-1}$ NMR (CDCl$_3$, δ): 0.89 (6H, t, J=7Hz), 1.12-1.34 (8H, m), 1.47-1.74 (4H, m), 2.04 (2H, t, J=7Hz), 2.96 (2H, t, J=7Hz), 5.31 (2H, s), 7.10 (1H, d, J=8Hz), 7.26 (1H, d, J=8Hz), 7.30 (1H, d, J=8Hz), 7.47 (1H, t, J=8Hz), 7.68-7.76 (3H, m)

The following compound was prepared according to a similar manner to that of Example 8.

EXAMPLE 50

5-(2-Carbamoylbenzyloxy)-2,2-dibutyl-3,4-dihydro-1(2H)-naphthalenone mp: 126°-127° C.

IR (Nujol): 3370, 3200, 1680, 1645, 1600, 1580, 1375, 1080, 1040 cm$^{-1}$

NMR (CDCl$_3$, δ): 0.85 (6H, t, J=7Hz), 1.22-1.32 (8H, m), 1.45-1.73 (4H, m), 2.00 (2H, t, J=7Hz), 2.93 (2H, t, J=7Hz), 5.32 (2H, s), 5.90 (1H, bs), 6.24 (1H, bs), 7.12 (1H, d, J=8Hz), 7.28 (1H, t, J=8Hz), 7.45 (1H, d, J=8Hz), 7.50 (1H, t, J=8Hz), 7.64-7.73 (3H, m)

We claim:

1. A bicyclic compound of the following formula:

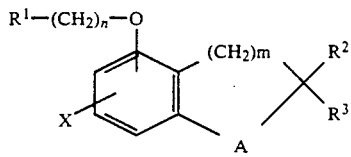

wherein

A is

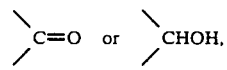

R$^1$ is benzothiazolyl which may have lower alkyl,

R$^2$ and R$^3$ are butyl,

X is hydrogen, halogen, hydroxy or lower alkyl, m is an integer 1 or 2, and n is an integer 1 to 4, or pharmaceutically acceptable salts thereof.

2. A compound according to claim 1, 2,2-dibutyl-5-(2-benzothiazolylmethoxy)-1,2,3,4-tetrahydro-1-naphthol.

3. An anti-inflammatory or anti-allergic pharmaceutical composition comprising an anti-inflammatory or anti-allergenic effective amount of a compound of the formula:

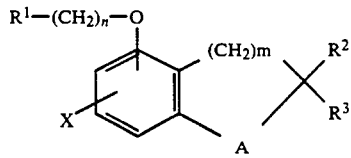

wherein

A is

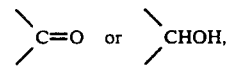

R$^1$ is benzothiazolyl which may have lower alkyl,

R$^2$ and R$^3$ are butyl,

X is hydrogen, halogen, hydroxy or lower alkyl, m is an integer 1 or 2, and n is an integer 1 to 4, or pharmaceutically acceptable salts thereof, in admixture with a pharmaceutically acceptable carrier.

4. An anti-inflammatory or anti-allergenic pharmaceutical composition according to claim 3, wherein the compound is 2,2-dibutyl-5-(2-benzothiazolylmethoxy)-1,2,3,4-tetrahydro-1-naphthol.

5. A method of treating inflammation or allergy in a subject in need thereof, which comprises administering to the subject an anti-inflammatory or anti-allergenic effective amount of a compound of the formula:

wherein

A is

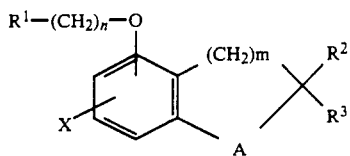

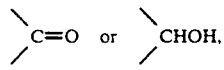

R[1] is benzothiazolyl which may have lower alkyl,
R[2] and R[3] are butyl,
X is hydrogen, halogen, hydroxy or lower alkyl,
m is an integer 1 or 2, and
n is an integer 1 to 4, or pharmaceutically acceptable salts thereof in admixture with a pharmaceutically acceptable carrier.

6. A method of treating inflammation or allergy as in claim 5, wherein the compound is 2,2-dibutyl-5-(2-benzothiazolylmethoxy)-1,2,3,4-tetrahydro-1-naphthol.

7. A method according to claim 5, for the treatment of asthma.

8. A method according to claim 6, for the treatment of asthma.